United States Patent [19]
Kuriyama et al.

[11] Patent Number: 5,767,271
[45] Date of Patent: Jun. 16, 1998

[54] LIGNAN GLYCOSIDES AND HYDROXY RADICAL SCAVENGERS

[75] Inventors: Kenichi Kuriyama, Yokohama; Tateo Murui, Tokyo, both of Japan

[73] Assignee: The Nisshin Oil Mills, Ltd., Tokyo, Japan

[21] Appl. No.: 577,933

[22] Filed: Dec. 22, 1995

[30] Foreign Application Priority Data

| Dec. 26, 1994 | [JP] | Japan | 6-336643 |
| Dec. 29, 1994 | [JP] | Japan | 6-338923 |
| Aug. 4, 1995 | [JP] | Japan | 7-219564 |
| Aug. 4, 1995 | [JP] | Japan | 7-219567 |

[51] Int. Cl.$^6$ ............ C07D 493/04; C07H 15/26
[52] U.S. Cl. ............ 536/128; 549/435; 252/404
[58] Field of Search ............ 536/128; 549/435; 252/404

[56] References Cited

U.S. PATENT DOCUMENTS

| 4,649,206 | 3/1987 | Namiki et al. | 549/435 |
| 5,314,812 | 5/1994 | Akimoto et al. | 435/134 |

FOREIGN PATENT DOCUMENTS

| 4-21475 | 4/1992 | Japan . |
| 5-124949 | 5/1993 | Japan . |
| 6-116282 | 4/1994 | Japan . |

OTHER PUBLICATIONS

"Science of Sesame", edited by M. Namiki et al. and published by Asakura Shoten, 1989, pp. 162–167.
Sugano et al., "Sesame Newsletter", 2, 3–9 (1993).
Katsuzaki et al., Biosci. Biotech. Biochem., 56, 2087–2088 (1992).
Fukuda et al., Japan Foods Industries Magazine 32, pp. 407 to 412 (1985).
Proceeding of 1991 Japan Society for Bioscience, Biotechnology, and Agrochemistry Meeting, p. 236, 1991.
Misra, H.P., Fridorich, I., Arch. Biochem. Biophs. 176, pp. 577 to 581, 1976.
Nathan, C.F., Siverstein, S.G., Brukner, L.H., and Cohen, Z.A., J. Exp. Med. 149, 100–113 (1979).
Biosci. Biotech. Biochem., 59, 1142–1143 (1995).

*Primary Examiner*—Nathan M. Nutter
*Attorney, Agent, or Firm*—Bacon & Thomas

[57] ABSTRACT

Lignan glycosides having a hydroxy radical scavenging activity and represented by the formula:

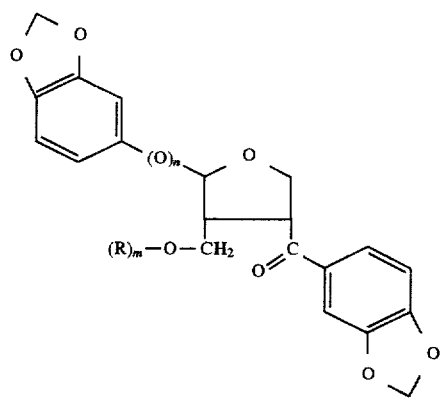

where R is a glycosyl residue selected from the group consisting of glucose, galactosr and fructose, m is an integer of 1 to 3, and n is 0 or 1.

13 Claims, 3 Drawing Sheets

MAGNETIC FIELD (mT)

LIGNAN GLYCOSIDES AND HYDROXY RADICAL SCAVENGERS

BACKGROUND OF THE INVENTION

1. Field of the Invention

The present invention relates to novel lignan glycosides and hydroxy radical scavengers comprising the same as an effective component.

2. Description of the Related Art

Lignans are defined as low molecular compounds produced by oxidative coupling of p-hydroxyphenylpropane units (see McCredie, R. S. et al., Aust. J. Chem., 22, 1011 (1969)). Lignans are relatively widely present in plants and contained in the cortex, xylem, seed and root of a plant. Up to now, more than 200 lignan compounds have been identified.

Many of lignans exhibit biological and/or physiological activities and their antibacterial or fungicidal, insecticidal, germination inhibiting, anti-tumor, platelet aggregating, anti-hypertension, antioxidant, active oxygen-eliminating, lipid metabolic, serum cholesterol-reducing, liver function-improving and/or immunologically activating actions have been reported (see, e.g., "Science of Sesame" edited by Mitsuo Namiki and Teisaku Kobayashi, Asakura Shoten, Japan, 1989).

For instance, sesamin (2,6-bis(3,4-methylenedioxyphenyl)-cis-3,7-dioxabicyclo[3.3.0]octane) having 3,7-dioxabicyclooctane ring, a typical lignan skeleton, and two methylenedioxyphenyl groups, which is a lignan contained in oily seeds such as sesame seeds, has recently been investigated for pharmacological effects and reported as remarkably exhibiting some of the aforementioned physiological actions (see, e.g., Michihiro Kanno and Kengo Akimoto, Sesame Newsletter, 2, 3, (1993)). It is believed that these physiological activities are attributed to the methylenedioxyphenyl or phenoxy groups in the lignan structure (see, e.g., "Science of Sesame" ibid.).

In addition to sesamin, a sesame seed also contains other phenolic lignans having an excellent anti-oxidant activity, such as sesaminol (tetrahydro-1-[6-hydroxy-3,4-(methylenedioxy)phenyl]-4-[3,4-(methylenedioxy)phenyl]-1H,3H-furo[3,4-c]furan), P-1 (tetrahydro-1-(3-methoxy-4-hydroxyphenyl)-4-[3,4-(methylenedioxy)phenyl]-1H,3H-furo[3,4-c]furan), sesamorinol(tetrahydro-1-[3-methoxy-4-hydroxyphenoxy]-4-[3,4-(methylenedioxy)phenyl]-1H,3H-furo[3,4-c]furan), and pinoredinol (tetrahydro-1,4-bis(3-methoxy-4-hydroxyphenyl)-1H,3H-furo[3,4-c]furan). It has been elucidated that many of them are present in the form of their glycosides in sesame seeds or defatted residues thereof (Biosci. Biotech. Biochem., 56, pp. 2087–2088, 1992). Pinoredinol glycosides are referred to in Japanese Patent Application Laying Open No. 6-116282 (1994) which shows that the pinoredinol glycosides have an anti-oxidant action against oxidation of lipids.

It has also been reported that phenolic anti-oxidant substances other than tocopherols and sesamol are produced in germinated sesame seeds (Journal of the Japanese Society For Food Science and Technology (or NIPPON SHOKU-HIN KOGYO GAKKAISHI), Vol. 32, pp. 407–412, 1985). Further, it is known that anti-oxidant or anti-photooxidation substances are extracted from cultured cells derived from adult sesame seeds (Proceedings of 1991 Japan Society for Bioscience, Biotechnology, and Agrochemistry Meeting (or NIPPON NOGEIKAGAKU KAISHI), p. 236, 1991; Japanese Patent Publication No. 4-21475 (1992); and Japanese Patent Application Laying Open No. 5-124949 (1993). However, all the substances disclosed in the publications are different from phenolic lignans as defined in the present invention.

The lignans are present predominantly in natural plants used for foods or medicinal purposes, such as sesame seeds; therefore, they can be said to be very safe compounds beneficial for human bodies.

When such functional compounds derived from natural materials are used for foods, pharmaceuticals and cosmetics, it is important to apply them under conditions enabling their useful functions to be effectively exhibited. For instance, when applied to human bodies, these compounds should not show adverse effects on the human bodies, such as toxicity, but they should advantageously have other good properties, such as emulsifiability and absorption.

However, many of lignans are highly oil-soluble due to their structure. For example, sesamin is soluble in non-aqueous organic solvents, such as chloroform and benzene, but insoluble in water. It is often advantageous that any compounds to be applied to living bodies are soluble in water or intermediately soluble in water and oil. Like lignans, almost water-insoluble, highly oil-soluble compounds can not sufficiently exhibit their effective phsiological performance to the living bodies even though they have such an effective performance.

SUMMARY OF THE INVENTION

Accordingly, it is an object of the present invention to provide a novel lignan compound which is expected to have some useful physiological activities, and which has a satisfactory water-solubility and therefore can be expected to be employed for foods, pharmaceuticals, agricultural chemicals and cosmetics.

According to the present invention, the above object and other objects which will be apparent from the following description are achieved by a lignan glycoside represented by the structural formula (I):

where R denotes a glycosyl residue selected from glucose, galactose and fructose, m denotes an integer of 1 to 3, and n is 0 or 1.

The lignan glycosides of the present invention are novel compounds which have not been described in published prior art references.

The lignan glycosides of the present invention have been found by the prsent inventors to have a hydroxy radical scavenging action. Accordingly, the present invention also provides a hydroxy radical scavenger comprising the lignan glycoside represented by the structural formula (I) above as an effective component.

DETAILED DESCRIPTION OF THE PREFERRED EMBODIMENTS

The lignan glycoside of the present invention is represented by the structural formula (I):

(I)

and believed to be a novel compound which has not been described in published prior art references. In the formula (I), R denotes a glycosyl residue selected from the group consisting of glucose, galactose and fructose residues, m denotes an integer of 1 to 3, and n is 0 or 1. Often, m is 2 or 3. As described hereinafter in detail, R is a glucose residue in the lignan glycosides extracted from humidified or germinated sesame seeds.

As seen in the structural formula (I), the lignan glycosides of the present invention are composed of a lipophilic aglycone moiety and a hydrophilic sugar moiety. The aglycone moiety has such a central skeleton that a 3,7-dioxabicyclooctane ring found in sesamin and sesaminol is cleaved between 3- and 4-positions, the carbon at 2-position constitutes a ketone, and the carbon at 4-position has a hydroxyl group to which a sugar moiety is linked. This central skeleton has two methylenedioxyphenyl groups which are considered in the art to be active sites responsible for various physiological activities of lignan.

The sugar moiety R of the lignan glycosides according to the present invention is constituted by 1 to 3 glucose, galactose or fructose residues.

Since the lignan glycosides of the present invention have both a lipophilic aglycone moiety and a hydrophilic sugar moiety as mentioned above, their solubility is approximately intermediate between water- and oil-solubility. For instance, they are excellent in compatibility with and permeability through biomembranes and may be advantageously used in the preparation of aqueous or emulsion-type foods or cosmetics.

As described in detail hereinafter, the lignan glycosides of the present invention scarcely exist in sesame seeds per se, although they may be derived from sesame seeds. However, their amounts increase in humidified or germinated sesame seeds, particularly largely in the early stage of germination. Such presence and phenomenon have been unknown.

Due to their steric structure, the lignan glycosides of the present invention are also biochemically stable, i.e., are not affected at all by the action of sugar chain hydrolases such as beta-glucosidase and cellulose. This is contrary to the fact that other known glycolipids and oligosaccharides, such as sesaminol glycosides and sterol glycosides, which have almost identical polarities and molecular weights with the said lignan glycosides and have been hitherto difficult to separate from the said glycosides, are easily hydrolyzed by the action of the said sugar chain hydrolases.

The present lignan glycosides represented by the formula (I) include those represented by the following formulae (II-a), (II-b) and (II-c), which are sometimes hereinafter referred to SG-1, SG-3 and SG-5, respectively:

(II-a)

where each Glc denotes a glucose residue;

(II-b)

where each Glc denotes a glucose residue; and (II-c)

where each Glc denotes a glucose residue.

The present lignan glycosides can be chemically synthesized but may conveniently be prepared from germinated sesame seeds as described below.

Sesame seed is a kind of oily seeds used for foods from old times and its pharmacological effects have been well known. Sesame is even now grown throughout the world, including the tropics, and eaten because of the unique favorite taste of its fats and oils and seed. Thus, sesame is one of relatively abundant and stably available plant materials and is safe to human bodies.

Irrespective of the nature, growing district and use, any sesame seeds may be used as starting materials for obtaining the lignan glycosides of the present invention provided that they do not undergo any high temperature treatment such as parching. Thus, there may be used any sesame seeds of white or black sesame; any sesame grown in Japan, China, India or Africa; or any sesame for culture or squeeze.

These sesame seeds are sowed uniformly in water or a suitable medium capable of retaining moisture, such as agar, quartz sand, sea sand, absorbent cotton, sand or soil, preferably in a sterilized medium, and cultured at a temperature of 10° to 50° C., preferably 30° to 40° C., with timely supplementing moisture, for 5 to 100 hours, preferably for 24 to 72 hours. The culture may be carried out either under light or in dark. By this procedure, the lignan glycoside of the present invention may be produced and accumulated in humidified or germinated sesame seeds.

The water-swollen or germinated sesame seeds are separated from the medium and then placed in a mill, such as a food mixer, blender or homogenizer. The milled materials may be treated with a oil-soluble organic solvent such as n-hexane to extract oily components out and the resultant defatted materials may be subjected to subsequent treatments.

Then, a lower alcohol with or without water capable of extracting the lignan glycosides is added to the milled materials or defatted materials thereof in an amount of 1 to 10 times (v/w) that of the latter wherein "v" and "w" used herein mean volume and weight, respectively. If necessary, the milling and extraction may be repeated. After conventional methods, such as decantation, centrifugation and filtration, are used to remove solids, water and alcohols are removed under normal or reduced pressures with or without heating to give a water-containing lower alcohol extract, which is a mixture comprising the lignan glycosides of the present invention and various sugar chain compounds.

Preferably, the water-containing lower alcohol used may be any mixture of water and a linear or branched lower alcohol having 1 to 4 carbon atoms, such as methanol, ethanol, n-propanol, isopropanol and n-butanol, with an alcohol concentration of 30 to 100% (v/v), preferably 50 to 100% (v/v), more preferably 50 to 80% (v/v), most preferably 70 to 80% (v/v). Alcohol concentrations less than 30% (v/v) are not preferred since large quantities of water-soluble polysaccharides which do not contain the lignan glycosides of the present invention are then extracted.

In order to remove impurities other than the lignan glycosides of the present invention i.e., oil-soluble and water-soluble materials, in the water-containing lower alcohol extract, this extract is desirably subjected to either (i) solvent-extraction or (ii) sugar chain hydrolase treatment followed by solvent-extraction.

In the treatment (i), a mixture of water and a water-insoluble organic solvent, such as chloroform or n-hexane, is first added to the water-containing lower alcohol extract in an amount of 2 to 10 times (v/w) that of the latter to extract oil-soluble impurities. After centrifugation into two phases, the organic phase is removed and aqueous phase is concentrated to dryness. The lignan glycosides of the present invention are concentrated into the aqueous phase.

Then, in order to remove water-soluble impurities, the extract is dispersed into a small amount, preferably 1 to 5 times (v/w) that of the extract, of a water-containing alcohol with an alcohol concentration of 30 to 100% (v/v) and this dispersion is dropwise added to a relatively large amount, preferably 10 to 200 times (v/w) that of the dispersion, of a gently stirred alcohol. After allowed to stand, the precipitates are removed by centifugation or fractional filtration and the filtrate is concentrated to dryness to give crude lignan glycosides. The alcohol used in this procedure may be such a lower alcohol as used in the aforementioned extracion of the milled sesame seeds. Alternatively, the extract may also be subjected to extraction with a water insoluble or slightly insoluble organic solvent having an intermediate polarity, such as n-butanol, ethyl acetate or methyl ethyl ketone, in an amount of 1 to 100 times (v/v) that of the extract to give similar crude lignan glycosides. These procedures may be repeated, if necessary.

In the treatment (ii), the water-containing lower alcohol extract is dispersed or dissolved in 1 to 100 times (v/w) of water or a buffer with a pH of 2 to 6. To this mixture, 0.1 to 30% (w/w), preferably 1 to 10% (w/w) of a sugar chain hydrolase is added and the sugar chain is hydrolyzed at 10° to 50° C. for 1 to 50 hours, preferably 5 to 15 hours, desirably with gently stirring. Instead of this sugar chain hydrolase, there may be used a water extract of milled, non-heated sesame seeds, which contains sugar chain hydrolase.

By this enzymatic reaction, almost of sterol glycosides, glycolipids, sesaminol glycosides, flavonoid glycosides and sugars, which have solvent distribution properties similar to those of the lignan glycosides of the present invention, are hydrolyzed to separate into more water-soluble sugars, such as monosaccharides and oligosaccharides, and aglycones (lignans). On the other hand, the lignan glycosides of the present invention are not affected or hydrolyzed by the action of such an enzyme due to the specificity of their steric structures.

The sugar chain hydrolases may include any enzymes hydrolyzing glucosyl or galactosyl residues, for example, glycosidases, such as commercially available beta-glucosidases, alpha-glucosidases, beta-galactosidases and alpha-galactosidases, and enzyme preparations, such as cellulases and amylases. As mentioned above, the sugar chain hydrolyzing activity of beta-glucosidase, alpha-galactosidase or cellulase, which is originally contained in the sesame seeds, can also be utilized. These enzyme preparations can be immobilized onto a suitable carrier, such as active carbon, celite, synthetic resin, ion-exchange resin or gel. Such immobilized enzyme preparations can be used continuously or recovered and recycled.

After the enzymatic reaction is completed, the reaction mixture is subjected to solvent extraction similar to the treatment (i) above to remove oil-soluble and water-soluble materials and any materials which are not hydrolyzed by the enzymic reaction are concentrated. More specifically, to the enzyme reaction mixture, 1 to 100 times (v/v) of a low porality, water-insoluble or slightly water-soluble organic solvent, such as n-hexane, chloroform, diethylether or petroleum ether, is added to extract and oil-soluble materials comprising fatty acid glycerides, phospholipids, lignans, sterols, and aglycons produced from glycosides other than the lignan glycosides of the present invention which are produced in the enzyme reaction are revomed as an organic solvent-phase.

Then, 1 to 100 times (v/v) of a slightly water soluble or water-insoluble organic solvent with an intermediate polarity, such as n-butanol, ethyl acetate or methyl ethyl ketone, is added to the remaining liquid (aqueous phase) and subjected again to extraction to remove water-soluble substances, such as sugars, proteins and fibrous materials, as an aqueous phase. The components extracted into this organic solvent phase are more highly polar than oil-soluble substances, such as sterols and lignans, and are not water-soluble unlike mono- and oligo-saccharides (that is, the materials which are not hydrolyzed by the afore-mentioned enzymatic reaction). These components are dried under vacuum to concentrate. Thus, an extract fraction containing a large amount of the lignan glycosides of the present invention (crude lignan glycoside) can be obtained.

Thus, the crude lignan glycosides obtained in each of the above treatments (i) and (ii) are mixtures of the substances represented by the structural formula (I). Their main components comprise at least one lignan glycosides represented by the structural formulae (II-a), (II-b) and (II-c).

The lignan glycosides of the formula (I) in which R is a galactose or fructose residue are also contained in the crude lignan glycosides obtained above through in a very small amount. These lignan glycosides can, however, be obtained in a large amount by a sugar addition reaction using the transglycosilation enzyme such as alpha- or beta-glucosidase, alpha- or beta-galactosidase, beta-d-fructofuranosidase, having a high glycosyl transferring activity, or a chemical reaction using a catalyst. When the enzymatic reaction is used, a transglycosilation enzyme capable of addition of galactosyl or fructosyl group is used. An acetohalogenation method which is widely used in the synthesis of oligosaccharides can be used to obtain lignan glycosides of the formula (I) in which R is a galactose or fructose residue. For example, the hydroxy groups of the lignan glycoside of the formula (I) in which R is a glucose residue as well as a galactose or fructose are acetohalogenated with acetic acid or hydrogen bromide, and are reacted with each other in the presence of a catalyst such as silver carbonate or mercury acetate to newly form glycoside linkages, thereby obtaining lignan glycosides of the formula (I) in which R is a galactose or fructose residue.

If necessary, the water-containing lower alcohol extracts and crude lignan glycosides can be fractionated and purified into individual lignan glycoside components using an adsorbent, such as silica gel or octadecyl silica (ODS). For example, after a column filled with ODS is equilibrated with water, the water-containing lower alcohol extracts or crude lignan glycosides are subjected at a loading rate of 0.1 to 5% (w/v) and certain fractions are eluted by the step-wise elution method in which the alcohol concentration is gradually increased using a water-containing alcohol solvent (the alcohol being methanol, ethanol, n-propanol, isopropanol or n-butanol). If necessary, the resultant eluted fractions can be further subjected to high performance liquid chromatography (HPLC) using said adsorbent or preparative liquid chromatography to further purify each component at a higher purity.

The chemical structure of the lignan glycosides can be confirmed by hydrolyzing each of highly purified single substances with e.g. an acid to separate into a lignan (aglycone) moiety and a sugar moiety and subjecting each of these to gas chromatography analysis after trimethylsilylation, or to other analysis, such as nuclear magnetic resonance spectroscopy or mass spectroscopy.

It has now been found that the lignan glycosides of the present invention have a hydroxy radical scavenging activity; i.e., decompose generated hydroxy radicals to extinguish them.

Organisms efficiently obtain energy required for their life by utilizing oxygen. In such energy metabolism, however, active oxygen species as intermediates are produced during the process for converting oxygen into water. Generally, the active oxygen species include superoxide anions released by stimulation of macrophages, hydroxy radicals produced by exposure to radiation, and organic radicals produced in association with peroxidation of lipids. These active oxygen species are high in chemical activity and reactive with lipids, nucleic acids and proteins causing oxidative injuries associated with various diseases. And, external inductors therefor are excessive radiation or ultraviolet irradiation, or intake of chemical substances or tobacco. Among these, for example, an important agent for living injuries caused by irradiation of radiation comprises hydroxy radicals produced from water molecules in the living bodies by the irradiation of radiation.

The hydroxy radical is one of the most reactive species among the active oxygen species and immediately reacts with lipids, proteins, nucleic acids or sugars present in the living bodies causing their oxidation, modification or decomposition. It is believed that genes, biomembranes and/or tissues are significantly injured thereby, causing various diseases, such as canceration, arteriosclerosis, heart diseases, inflammation and cell ageing (Halliwell B. and Gutteridge M. C., Biochem. J., Vol. 219, pp. 1–14 (1984)).

Accordingly, any substances having a function of efficiently scavenging or eliminating such toxic active oxygen species are useful as agents for controlling oxidative degradation of components present in living bodies, foods, and medical and agricultural chemicals, and expected to be practically used in food fields, such as healthy and nutrient foods, pharmaceutical fields, agricultural chemical fields, and cosmetics fields. Many of the known anti-oxidants, such as tocopherols and ascorbic acid are still unknown to have a hydroxy radical scavenging ability, except vitamin E which has the activity.

Recently, as the toxicity of such active oxygen species, in particular hydroxy radicals, to living bodies is been elucidated, an attention has been paid to the utility of substances which may efficiently scavenge or eliminate the radicals and various substances, in particular nature-derived materials have been investigated. Typical examples typically having a hydroxy radical scavenging activity include mannitol, tryptophan, and formic acid and these hydroxy radical scavenging effect is now been investigated (See, for example. Misra, H. P., Fridovich, I., Arch. Biochem. Biophs. 176, 577–581 (1976); and Nathan, C. F., Silverstein, S. G., Brukner, L. H., and Cohen, Z. A., J. Exp. Med., 149, 100–113 (1979).

However, there are few substances which show practically effective hydroxy radical scavenging activity at a very small amount and it is now difficult to obtain such substances at large amounts industrially and stably. Thus, stable supply of effective ingredients having a hydroxy radical scavenging activity has scarcely been brought into practice industrially though highly desirable.

Hydroxy radical scavenging activities may be determined by the spin trap method using 5,5'L-dimethyl-1-pyrroline-N-oxide (DMPO) in an electron spin resonance (ESR) apparatus: see, for example, Gow-Chin Yen and Pin-Der Cuh, J. Agric. Food Chem., Vol. 42, pp. 629–632, (1994).

Hydroxy radicals and hydroxy anions are produced from hydrogen peroxide through Fenton reaction in the presence of a ferrous sulfate solution. The hydroxy radicals are trapped by the coexisting DMPO to form DMPO-OH adducts. This adduct is relatively stable and exhibits a characteristic quartet in an ESR spectrum. If any substance having an activity of eliminating or scavenging a hydroxy radical coexists in the reaction liquid, the ESR spectrum of DMPO-OH adduct will be reduced. A hydroxy radical scavenging activity of a sample can be determined from the reduced amount of integrated value of the spectrum.

The afore mentioned references investigated the hydroxy radical scavenging activities of mannitol, tryptophan and formic acid as substances having an activity of scavenging hydroxy radicals. These activities were measured at concentrations of 10 µmol/mL for mannitol, 20 µmol/mL for tryptophan, and 100 µmol/mL for formic acid. In the present invention, on the contrary, the lignan glycosides may show sufficient hydroxy radical scavenging activities even at a very small amount of 1 µmol/mL or below. Thus, the lignan glycosides of the present invention have a very high hydroxy radical scavenging activity.

The hydroxy radical scavenger according to the present invention may comprise, as an effective ingredient, at least one of the lignan glycosides represented by the structural formula (I), in particular di- and/or triglucoside lignans represented by the structural formula (I), and the lignan glycosides represented by the structural formulae (II-a), (II-b) and (II-c). These lignan glycosides may be chemically synthesized, or may be the aforementioned water-containing lower alcohol extracts obtained from humidified or germinated sesame seeds, or the crude lignan glycosides obtained by removing oil-soluble and water-soluble materials from said extracts which have optionally been treated with a sugar chain hydrolase. Preferably, higher purity lignan glycosides obtained from fractionating the extracts or crude lignan glycosides by column chromatography or HPLC are used.

The present invention will be illustrated by the following non-limiting examples.

Example 1

Previously sterilized quartz sand was spread in a stainless vat of 300 cm$^2$ in inner volume and 10 g of sesame seeds from China were sowed thereon. While distilled water was thoroughly sprayed, the seeds were incubated in a thermostat at 40° C. for 2 days to germinate. The proportion of seeds germinated was 89% or higher. A certain amount of germinated seeds in similar germinating states was milled with 100 ml of a water-containing methanol (80% (v/v)) in a blender. The residue was filtered and the filtrate was concentrated to dryness to give a water-containing methanol extract. Then, the extract was washed and extracted with n-hexane to remove oil-soluble materials and then washed and extracted with water-saturated n-butanol to remove water-soluble materials to give a crude lignan glycoside. This crude lignan glycoside was re-dissolved in 100 ml of water-containing methanol (80% (v/v)) and subjected to high performance liquid chromatography (HPLC) to analyze the composition.

The HPLC was carried out by connecting a column (Soken Pak ODS-W 5µ, 10 mm φ×250 mm, product by Soken Kagaku Ltd., Japan) and an ultraviolet absorption detector (UV-8000, manufactured by Toso, Japan) to a pump (CCPM, manufactured by Toso, Japan), eluting with a linear gradient of water:methanol from 90:10 (v:v) to 10:90 (v:v) after 60 minutes at a flow rate of 1 ml/min., and using a detection wave length at 280 nm.

HPLC was carried out to determine the composition and content of the novel lignan glycosides in the crude lignan glycoside using sesamin as an external standard. As a result, the crude lignan glycoside comprised 115 mg in total of 30% by weight of SG-1 (formula II-a), 40% by weight of SG-3 (formula II-b) and 30% by weight of SG-5(formula II-c).

The chemical structure of each lignan glycoside component was confirmed in the following manner, using each single component from the highly purified products through the preparative HPLC under the aforementioned conditions. Thus, 1N hydrochloric acid was added to each of the purified products to hydrolyzed at 100° C. for 30 minutes, after which the reaction mixture was extracted with ethyl acetate and separated into an ethyl acetate and aqueous layers. The ethyl acetate layer was concentrated to dryness at 40° C. or below, trimethylsilylated with TMS-PZ (Tokyo Kasei Kogyo Corporation), and subjected to gas chromatography (GLC) to quantitatively determine lignans using sesamin as an external standard.

The GLC conditions were as follows. GLC Apparatus: Hewlett-Packard Co. 5890; column: DB-17HT (15 m×0.319 mm, film thickness: 0.15 µm, J & W SCIENTIFIC Cor.; injection: split type (split ratio of 1/10); column temperature: 270° C.; anc carrier gas: Helium.

The aqueous layer was filtered through an HPLC pretreatment filter (pore size: 0.2 µm, Myshori Desk W-13-2, Toso, Japan) and the filtrate was mixed with 5 ml of acetone, concentrated to dryness under reduced pressure, trimethylsilylated with TMS-PZ (same as above), and subjected to GLC to quantitatively determine the sugars (external standard: glucose, galactose, fructose).

The GLC conditions were the same as in the aforementioned lignan analysis except that the column used was DB-1701 (15 m×0.25 mm, the film thickness was 1.0 µm (J & W SCIENTIFIC Cor.) the injection was split type (split ratio of 1/50), and the column temperature was 180° C.

The ultraviolet and infrared absorption spectra data of SG-1, SG-3 and SG-5 were as follows:

SG-1: UV lamda max (methanol solution, MeOH) nm (log epsilon) 230 (4.10); 281 (3.74) and 311 (3.66).

IRv:(cm$^{-1}$) (assignment) 3400 (OH); 2950 (CH); 1670; 1620; 1505; 1500; 1450 (aromatic ring, Ar); 1260 (Ar-O-C) and 1040 (C-O-C).

SG-3: UV lamda max (MeOH) nm (log epsilon) 230 (4.00); 280 (3.60) and 310 (3.50).

IRv: (cm$^{-1}$) (assignment) 3400 (OH); 2900 (CH); 1660; 1610; 1510; 1490; 1450 (Ar); 1260 (Ar-O-C) and 1040 (C-O-C).

SG-5: UV lamda max (MeOH) nm (log epsilon) 231 (4.22); 280 (3.81) and 299 (3.83).

IRv: (cm$^{-1}$) (assignment) 3400 (OH); 2900 (CH); 1670; 1510; 1490; 1450 (Ar); 1260 (Ar-O-C) and 1040 (C-O-C).

Figure 1:
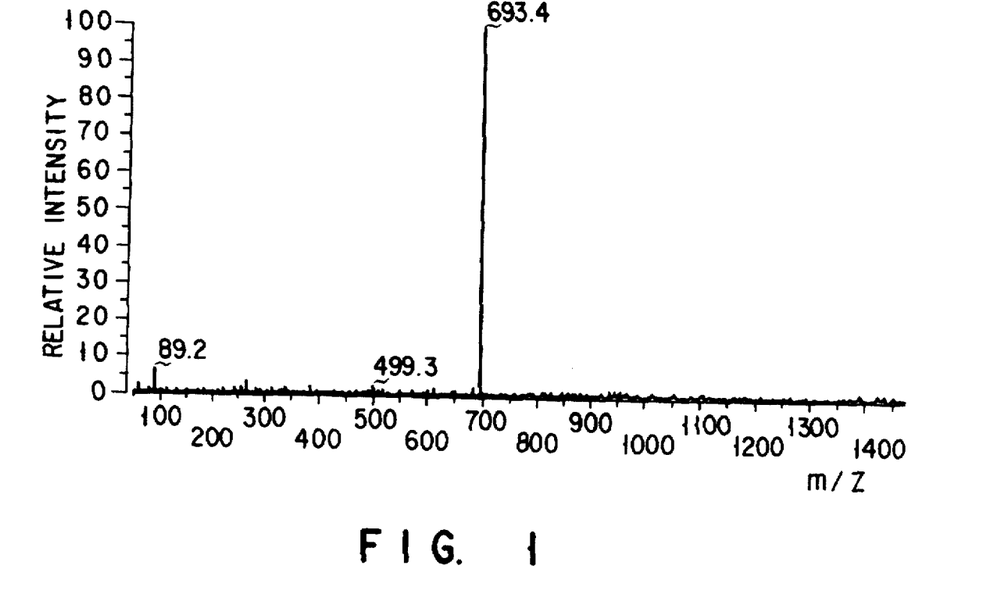
FIG. 1 is a high resolution mass spectrum of a lignan glycoside of the present invention.
Figure 2:
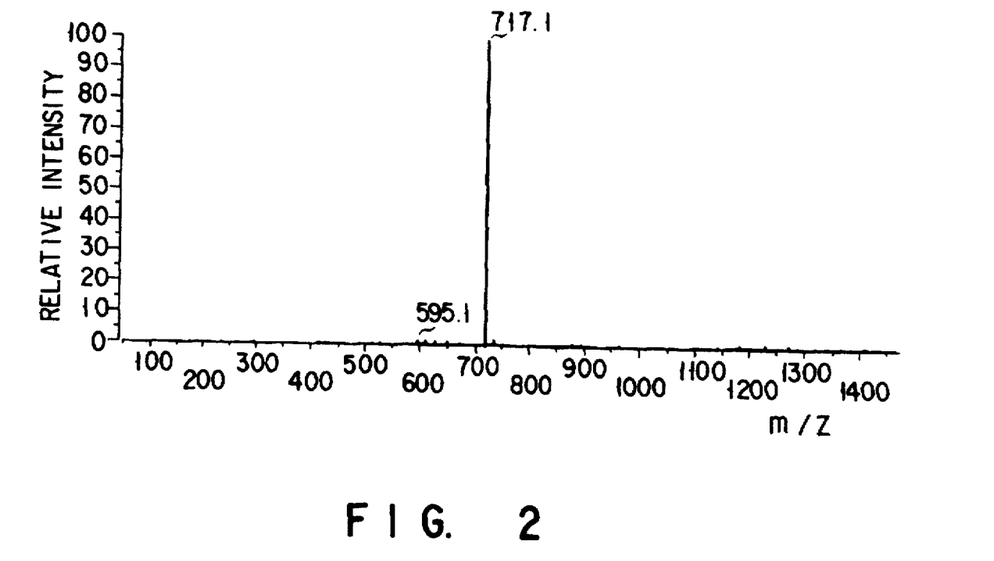
FIG. 2 is a high resolution mass spectrum of a sodium adduct of the said lignan glycoside.
Figure 3A:
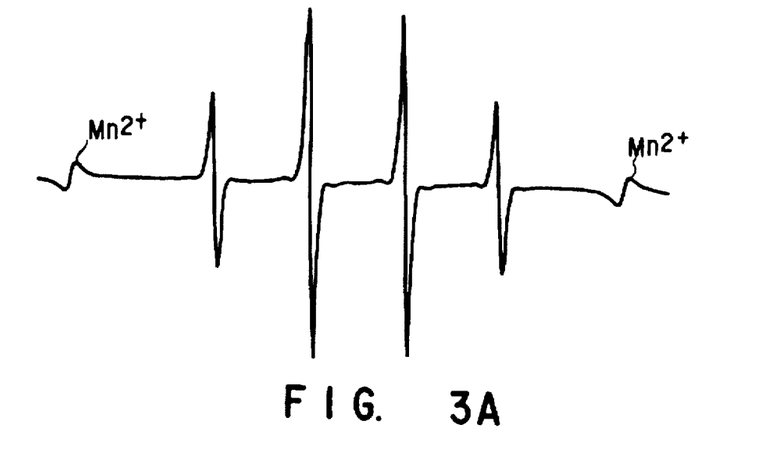
FIGS. 3A, 3B, 3C and 3D are graphs which show the change of the hydroxy radical scavenging activity versus the added amounts of the lignan glycoside according to the present invention.
Figure 3B:
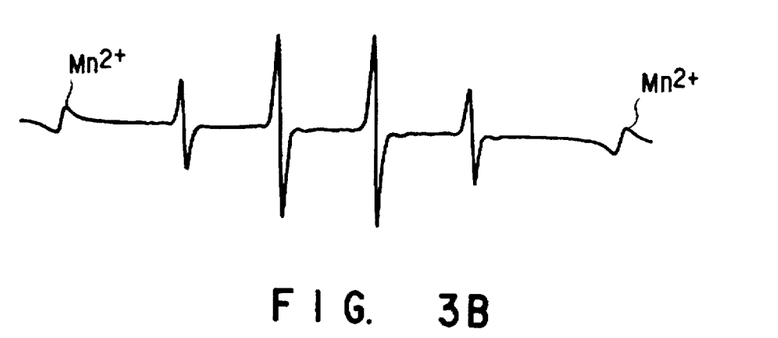
Figure 3C:
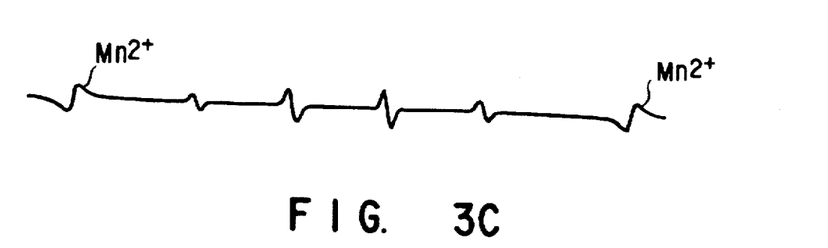
Figure 3D:
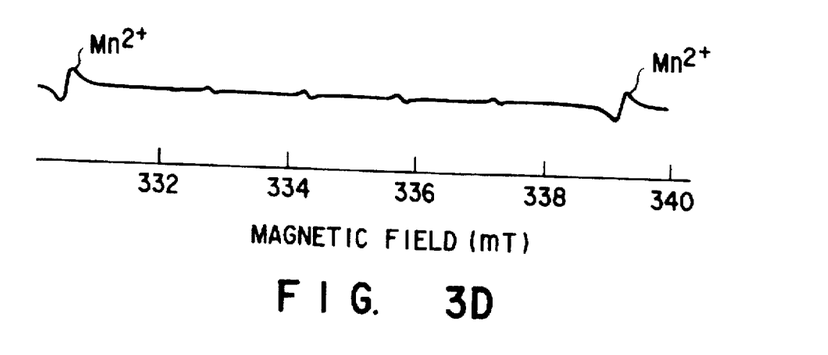

Each of the lignan glycosides was subjected to mass analysis. For example, SG-3 showed mass spectra as shown in FIGS. 1 and 2. The spectra of the corresponding sodium adduct ion (m/z 717.1) and molecular ion (m/z 693.4) were explicitly detected as shown in FIGS. 2 and 1, respectively. The molecular weights of SG-1, SG-3 and SG-5 were determined to be 856, 694 and 710, respectively.

The results of nuclear magnetic resonace spectra ($^{13}$C-NMR) of SG-1, SG-3 and SG-5 were as follows:

SG-1: 198.4; 151.9; 148.0; 147.6; 147.0; 135.2; 131.9; 124.8; 119.6; 107.4; 107.3; 107.2; 106.2; 103.7; 103.2; 101.7; 100.6; 100.9; 82.7; 81.5; 76.3; 76.1; 75.7; 75.5; 74.8; 74.4; 73.2; 69.7; 69.6; 69.5; 69.4; 68.3; 65.7; 60.9; 60.7; 51.3 and 46.7.

SG-3: 198.3; 152.0; 148.1; 147.6; 147.0; 135.2; 131.8; 124.8; 119.6; 107.3; 107.2; 107.1; 106.2; 103.8; 101.1; 101.7; 100.6; 82.8; 81.6; 76.3; 76.3; 75.7; 75.7; 74.4; 69.6; 69.5; 69.4; 65.7; 60.8; 60.8; 51.3 and 46.7.

SG-5: 195.9; 151.8; 151.2; 148.2; 147.8; 142.4; 131.3; 124.5; 108.5; 107.4; 107.1; 107.1; 105.4; 103.5; 101.8;

100.7; 100.6; 99.3; 81.3; 76.3; 76.3; 75.9; 75.9; 74.0; 69.3; 69.3; 67.9; 65.0; 60.7; 60.7; 48.7 and 45.1.

Example 2

A water-containing methanol extract obtained in the same manner as in Example 1 was dispersed 100 mL of 20 mM acetic acid buffer (pH 5.0) and 200 mg of beta-glucosidase (Funakoshi), 1 g of cellulase (Boeringer-Manheim) and 1 g of amylase (Wako Junyaku) were added and shaken at 50° C. for 15 hours. The same volume of n-hexane was added to the reaction liquid and vigorously shaken. This extraction procedure was repeated three times to remove oil-soluble materials. To the remaining liquid from which the n-hexane phase was completely removed, the same volume of n-butanol previously saturated with water was added and vigorously shaken. This extraction procedure was repeated twice to remove water-soluble materials. The n-butanol phase was twice washed with the same volume of distilled water and concentrated to dryness under reduced pressure to yield a crude lignan glycoside.

The crude lignan glycoside was analyzed by HPLC in the same manner as in Example 1 to find that the crude product contained about 150 mg of novel lignan glycosides which comprised 24% by weight of SG-1, 43% by weight of SG-3, and 33% by weight of SG-5.

Example 3

A crude lignan glycoside obtained by the method as described in Example 1 was subjected to partition chromatography on ODS as a carrier. A glass column of 3 cm in diameter and 50 cm in length was filled with 60 g of YMC-GEL ODS-A (Yamamura Kagaku K. K.) and equilibrated with water. The crude lignan glycoside (1 g) was loaded on the top of the column. The eluent in which the concentration of methanol in water was gradually increased was used in a stepwise elution method to elute fractions. Those fractions eluted with 30 to 60% (v/v) methanol were collected and concentrated to dryness to yield about 100 mg of column fractions.

The fractions were repeatedly subjected to preparative HPLC to purify until each of the lignan glycosides was obtained as a single component. As a result, purified lignan glycosides, SG-1, SG-3 and SG-5 were obtained each in an amount of 5 to 10 mg. The content of the whole lignan glycoside components was 2.5% (w/w) based on the dried germinated seeds and 5.0% (w/w) based on the water-containing methanol extract.

Example 4

The hydroxy radical eliminating activities of the lignan glycoside components were determined. Thus, the hydroxy radical eliminating activities were determined by spin trap method with DMPO in an electron spin resonance (ESR) apparatus. The reaction mixture consisted of 75 µl of 0.1 mM ferrous sulfate solution containing 0.55 mM diethylenetriamine N,N,N',N'',N''-pentaacetic acid, 75 µl of 1 mM hydrogen peroxide solution, 20 µl of 8.8 mM DMPO solution, and 50 µl of an aqueous solution of each of the following lignan glycosides. The purified product SG-3 obtained in Example 3 was added to the reaction mixture at a predetermined concentration in the range of 0 to 1.0 µmol/ml and each spectrum of DMPO-OH adduct was determined in the ESR apparatus. The ESR determination was carried out in an ESR apparatus (JEOL Ltd., JES-REIX) under the conditions: magnetic field of 334.5±5 mT, output of 8 mV, modulation of 100 kHz and response time of 0.1 s at room temperature using manganese ion ($Mn^{2+}$) in magnesium oxide as a standard. The ESR spectra of hydroxy radical eliminating activity of SG-3 are shown in FIGS. 3A to 3D. As the concentration of SG-3 added increased, the spectrum was clearly reduced (FIGS. 3B, 3C and 3D) as compared with the ESR spectrum of FIG. 3A in which no SG-3 was added. Thus, it was found that SG-3 has an activity of eliminating hydroxy radicals.

Example 5

Figure 4:
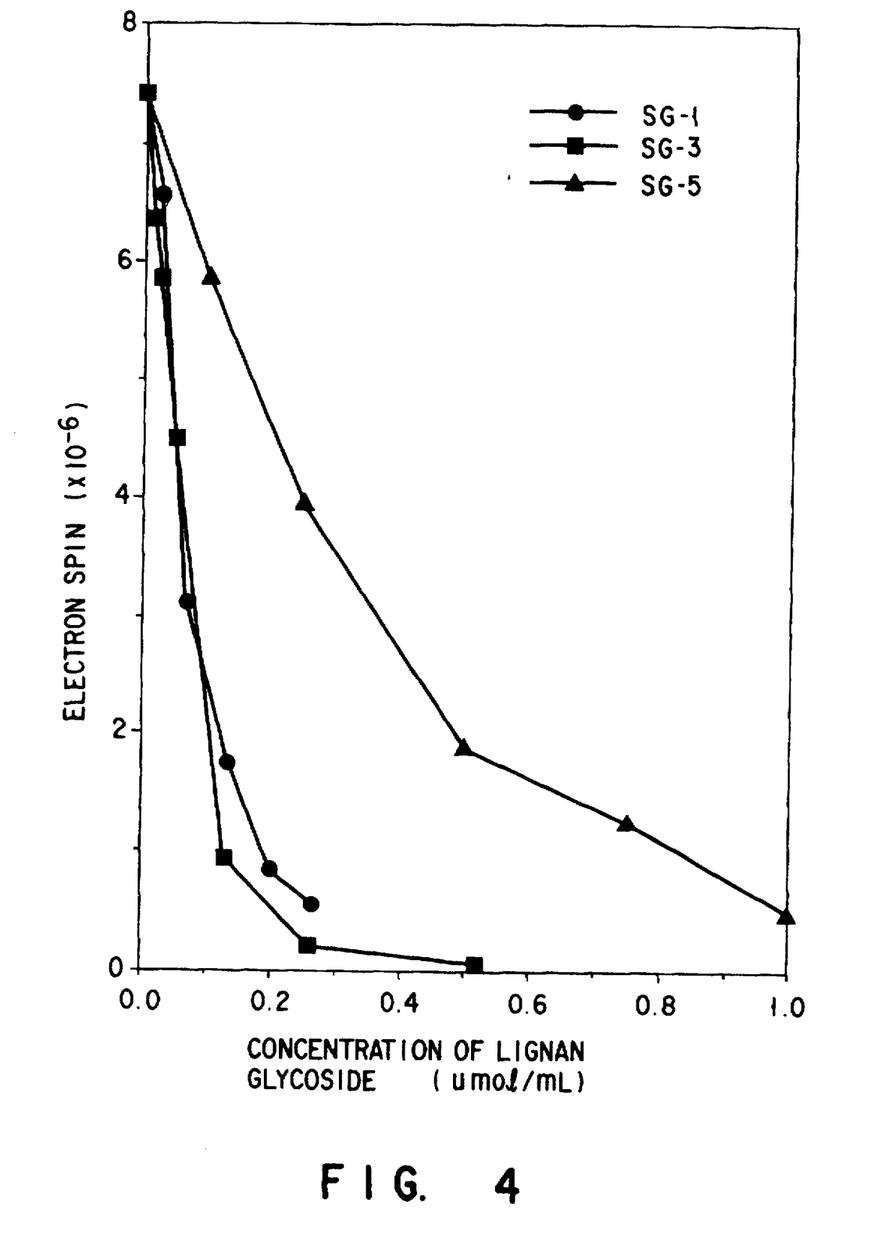
FIG. 4 is a graph which shows the relationship between the hydroxy radical scavenging activity and the added amounts of the lignan glycoside according to the present invention.

In the method described in Example 4, the ESR spectra were measured with different lignan glycoside components (purified products of SG-1 and SG-5 obtained in Example 3) added to the reaction mixture for measuring hydroxy radicals at different concentrations and the relationship between the integrated value and the concentration added was investigated for each glycoside component. As shown in FIG. 4, a strong activity of eliminating hydroxy radicals was observed in all the reaction mixtures containing 0.01 to 1.0 µmol/ml of lignan glycoside component SG-1, SG-3 or SG-5.

Example 6

The water-containing methanol extracts (a) and crude lignan glycosides (b) obtained in Example 1, the crude lignan glycosides (c) obtained in Example 2, and the column fractions (d) obtained in Example 3 were each used as samples to determine the hydroxy radical eliminating activities in the same manner as described in Example 4. The concentration of each sample at which 50% of the hydroxy radical intensity at no addition of sample was eliminated was (a) 30 µmol/ml, (b) 2 µmol/ml, (c) 1 µmol/ml and (d) 0.1 µmol/ml. Thus, it was found that the lignan glycosides (SG-1, SG-3 and SG-5) have sufficient hydroxy radical eliminating capability not only alone but also in any mixtures thereof.

As stated, the present invention provides a lignan glycoside represented by the structural formula (I). The lignan glycoside may be readily obtained from germinated sesame seeds. The hydroxy radical scavenger of the present invention comprising the lignan glycoside represented by the structural formula (I) as an effective ingredient exhibits a strong hydroxy radical eliminating capability at a very small amount and is expected to be applied to products in the food, cosmetic, medicine and agrichemical fields.

What is claimed is:

1. A lignan glycoside represented by the formula:

where R is a glycosyl residue selected from the group consisting of glucose, galactose and fructose, m is an integer of 1 to 3, and n is 0 or 1.

2. The lignan glycoside of claim 1, wherein $(R)_m$ is a diglycide or triglycide.

3. A lignan glycoside represented by the formula (II-a):

where each Glc is a glucose residue.

4. A lignan glycoside represented by the formula (II-b):

where each Glc is a glucose residue.

5. A lignan glycoside represented by the formula (II-c):

where each Glc is a glucose residue.

6. A hydroxy radical scavenger comprising at least one lignan glycoside represented by the formula:

where R is a glycosyl residue selected from the group consisting of glucose, galactose and fructose, m is an integer of 1 to 3, and n is 0 or 1, as an effective ingredient.

7. The hydroxy radical scavenger of claim 6, wherein (R)$_m$ is a diglycide or triglycide.

8. The hydroxy radical scavenger of claim 6, wherein the lignan glycoside is represented by the formula (II-a):

where each Glc is a glucose residue.

9. The hydroxy radical scavenger of claim 6, wherein the lignan glycoside is represented by the formula (II-b):

where each Glc is a glucose residue.

10. The hydroxy radical scavenger of claim 6, wherein the lignan glycoside is represented by the formula (II-c):

(II-c)

where each Glc is a glucose residue.

11. A hydroxy radical scavenger comprising, as an effective ingredient, a lignan glycoside-containing material obtained by extracting a milled material of a humidified or germinated sesame seed or a defatted material thereof with a water-containing lower alcohol having 1 to 4 carbon atoms and removing oil-soluble and water-soluble materials from the extract.

12. A hydroxy radical scavenger comprising, as an effective ingredient, a lignan glucoside-containing material obtained by extracting a milled material of a humidified or germinated sesame seed or a defatted material thereof with a water-containing lower alcohol having 1 to 4 carbon atoms, treating the extract with a sugar chain hydrolase in an aqueous medium, removing oil-soluble and water-soluble materials from the unhydrolyzed product, and concentrating it.

13. The hydroxy radical scavenger of claim 12, wherein the sugar chain hydrolase is at least one of alpha-glucosidases, beta-glucosidases, alpha-galactosidases, beta-galactosidases, cellulases and amylases.

* * * * *